(12) United States Patent
Watson et al.

(10) Patent No.: US 10,226,188 B2
(45) Date of Patent: Mar. 12, 2019

(54) SYSTEMS AND METHODS FOR MONITORING BLOOD PRESSURE

(71) Applicant: Covidien LP, Mansfield, MA (US)

(72) Inventors: James Watson, Dunfermline (GB); Keith Manning, Linlithgow (GB); Paul S. Addison, Edinburgh (GB)

(73) Assignee: Covidien LP, Mansfield, MA (US)

( * ) Notice: Subject to any disclaimer, the term of this patent is extended or adjusted under 35 U.S.C. 154(b) by 1384 days.

(21) Appl. No.: 13/974,292

(22) Filed: Aug. 23, 2013

(65) Prior Publication Data

US 2015/0057554 A1 Feb. 26, 2015

(51) Int. Cl.
*A61B 5/021* (2006.01)
*A61B 5/00* (2006.01)
*A61B 5/022* (2006.01)
*A61B 5/024* (2006.01)

(52) U.S. Cl.
CPC ........ *A61B 5/02125* (2013.01); *A61B 5/7221* (2013.01); *A61B 5/7246* (2013.01); *A61B 5/02241* (2013.01); *A61B 5/02416* (2013.01); *A61B 5/7214* (2013.01)

(58) Field of Classification Search
CPC ..................................................... A61B 5/021
USPC ......................................................... 600/485
See application file for complete search history.

(56) References Cited

U.S. PATENT DOCUMENTS 6,135,966 A 10/2000 Ko
6,178,343 B1 1/2001 Bindszus et al.
6,293,915 B1 9/2001 Amano et al.
6,449,501 B1 9/2002 Reuss
6,599,251 B2 7/2003 Chen et al.
6,675,031 B1 1/2004 Porges et al.
6,684,090 B2 1/2004 Ali et al.

(Continued)

FOREIGN PATENT DOCUMENTS

JP 2007020836 A 2/2007
WO 9843071 A1 10/1998

OTHER PUBLICATIONS

"Detection of motion artifacts in photoplethysmographic signals based on time and period domain analysis" by Couceiro et al., 34th Annual International Conference of the IEEE EMBS, San Diego, California USA, 2012.*

(Continued)

*Primary Examiner* — Etsub Berhanu
(74) *Attorney, Agent, or Firm* — Fletcher Yoder PC

(57) ABSTRACT

Various methods and systems for blood pressure monitoring are provided. A device for monitoring blood pressure may include a memory storing instructions for receiving one or more signals representative of one or more patient parameters, wherein at least one of the one or more signals comprises a plethysmography signal. The memory also stores instructions for determining a change in a pulse shape metric of the plethysmography signal and determining a change in a blood pressure signal over a period of time based on the one or more signals. The memory also stores instructions for determining a confidence level of the blood pressure signal based at least in part on a correlation between the change in the blood pressure signal and the change in the pulse shape metric over the period of time. The device also includes a processor configured to execute the instructions.

18 Claims, 8 Drawing Sheets

(56) References Cited

U.S. PATENT DOCUMENTS

| | | |
|---|---|---|
| 6,725,074 B1 | 4/2004 | Kastle |
| 6,996,427 B2 | 2/2006 | Ali et al. |
| 7,006,856 B2 | 2/2006 | Baker, Jr. et al. |
| 7,024,233 B2 | 4/2006 | Ali et al. |
| 7,074,192 B2 | 7/2006 | Friedman et al. |
| 7,186,217 B2 | 3/2007 | Kawasaki |
| 7,376,238 B1 | 5/2008 | Rivas et al. |
| 7,390,300 B2 | 6/2008 | Inukai et al. |
| 7,390,301 B2 | 6/2008 | Skrabal et al. |
| 7,393,327 B2 | 7/2008 | Inukai et al. |
| 7,455,643 B1 | 11/2008 | Li et al. |
| 8,123,695 B2 | 2/2012 | Baker, Jr. |
| 8,221,326 B2 | 7/2012 | Baker, Jr. |
| 2003/0031280 A1 | 2/2003 | Rouphael |
| 2004/0097797 A1 | 5/2004 | Porges et al. |
| 2004/0133087 A1 | 7/2004 | Ali et al. |
| 2004/0138538 A1 | 7/2004 | Stetson |
| 2004/0138540 A1 | 7/2004 | Baker, Jr. et al. |
| 2005/0148885 A1 | 7/2005 | Tweed et al. |
| 2005/0261594 A1 | 11/2005 | Banet |
| 2006/0009700 A1 | 1/2006 | Brumfield et al. |
| 2006/0030764 A1 | 2/2006 | Porges et al. |
| 2006/0030766 A1 | 2/2006 | Stetson |
| 2006/0063992 A1 | 3/2006 | Yu et al. |
| 2006/0063993 A1 | 3/2006 | Yu et al. |
| 2007/0073124 A1 | 3/2007 | Li et al. |
| 2007/0179369 A1 | 8/2007 | Baker, Jr. |
| 2008/0146901 A1 | 6/2008 | Katura et al. |
| 2008/0214942 A1 | 9/2008 | Oh et al. |
| 2008/0242955 A1 | 10/2008 | Uutela et al. |
| 2008/0269624 A1 | 10/2008 | Zhang et al. |
| 2008/0287814 A1 | 11/2008 | Meuhsteff et al. |
| 2009/0326386 A1 | 12/2009 | Sethi et al. |
| 2010/0249549 A1 | 9/2010 | Baker, Jr. et al. |
| 2010/0332173 A1 | 12/2010 | Watson et al. |
| 2012/0059267 A1* | 3/2012 | Lamego ............ A61B 5/021 600/483 |
| 2012/0136605 A1* | 5/2012 | Addison ............ A61B 5/02125 702/98 |
| 2012/0143067 A1 | 6/2012 | Watson et al. |
| 2013/0137936 A1 | 5/2013 | Baker, Jr. et al. |

OTHER PUBLICATIONS

International Search Report and Written Opinion for PCT Application PCT/US2014/052047 dated Nov. 24, 2014; 9 pgs.

Barnum, P.T., et al.; "Novel Pulse Oximetry Technology Capable of Reliable Bradycardia Monitoring in the Neonate," Respiratory Care, vol. 42, No. 1, p. 1072 (Nov. 1997).

Pickett, John, et al.; "Pulse Oximetry and PPG Measurements in Plastic Surgery," Proceedings—19th International Conference—IEEE/EMBS, Chicago, Illinois, Oct. 30-Nov. 2, 1997, pp. 2330-2332.

East, Christine E., et al.; "Fetal Oxygen Saturation and Uterine Contractions During Labor," American Journal of Perinatology, vol. 15, No. 6, pp. 345-349 (Jun. 1998).

Seelbach-Gobel, Birgit, et al.; "The prediction of fetal acidosis by means of intrapartum fetal pulse oximetry," Am J. Obstet. Gynecol., vol. 180, No. 1, Part 1, pp. 73-81 (1999).

Shamir, M., et al.; "Pulse oximetry plethysmographic waveform during changes in blood volume," British Journal of Anaesthesia 82(2): 178-81 (1999).

Nilsson, Lena, et al.; "Monitoring of Respiratory Rate in Postoperative Care Using a New Photoplethysmographic Technique," Journal of Clinical Monitoring and Computing, vol. 16, pp. 309-315 (2000).

Belal, Suliman Yousef, et al.; "A fuzzy system for detecting distorted plethysmogram pulses in neonates and paediatric patients," Physiol. Meas., vol. 22, pp. 397-412 (2001).

Maletras, Francois-Xavier, et al.; "Construction and calibration of a new design of Fiber Optic Respiratory Plethysmograph (FORP)," Optomechanical Design and Engineering, Proceedings of SPIE, vol. 4444, pp. 285-293 (2001).

Earthrowl-Gould, T., et al.; "Chest and abdominal surface motion measurement for continuous monitoring of respiratory function," Proc. Instn Mech Engrs, V215, Part H; pp. 515-520 (2001).

Lutter, Norbert O., et al.; "False Alarm Rates of Three Third-Generation Pulse Oximeters in PACU, ICU and IABP Patients," Anesth Analg, vol. 94, pp. S69-S75 (2002).

Yoon, Gilwon, et al.; "Multiple diagnosis based on Photo-plethysmography: hematocrit, SpO2, pulse and respiration," Optics in Health Care and Biomedical optics: Diagnostics and Treatment; Proceedings of the SPIE, vol. 4916; pp. 185-188 (2002).

Johansson, A.; "Neural network for photoplethysmographic respiratory rate monitoring," Medical & Biological Engineering & Computing, vol. 41, pp. 242-248 (2003).

Johnston, W.S., et al.; "Extracting Breathing Rate Infromation from a Wearable Reflectance Pulse Oximeter Sensor," Proceedings of the 26th Annual International conference of the IEEE EMBS, San Francisco, California; Sep. 1-5, 2004; pp. 5388-5391.

Spigulis, Janis, et al.; "Optical multi-channel sensing of skin blood pulsations," Optical Sensing, Proceedings of SPIE, vol. 5459, pp. 46-53 (2004).

Gesquiere, Michael J., et al., "Impact of withdrawal of 450 ML of blook on respiration-induced oscillations of the ear plethysmographic waveform," Journal of Clinical Monitoring and Computing (2007) 21:277-282.

Wu, Dongmei, et al.; "Na*/H* Exchange inhibition delays the onset of hypovolemic circulatory shock in pigs," Shock, vol. 29, No. 4, pp. 519-525 (2008).

Chen, Liangyou, et al.; "IS respiration-induced variation in the photoplethysmogram associated with major hypovolemia in patients with actue tramatic injuries," Shock, vol. 34, No. 5, pp. 455-460 (2010).

McGrath, S.P., et al.; "Pulse oximeter plethysmographic waveform changes in awake, spontaneously breathing, hypovolemic volunteers," Anesth. Analg. vol. 112 No. 2, pp. 368-374 (2010).

* cited by examiner

SYSTEMS AND METHODS FOR MONITORING BLOOD PRESSURE

BACKGROUND

The present disclosure relates generally to medical devices, and, more particularly, to systems and methods for monitoring blood pressure of a patient.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. In some cases, clinicians may wish to monitor a patient's blood pressure. Blood pressure may be assessed using a wide variety of monitoring devices. For example, blood pressure may be monitored non-invasively via a sphygmomanometer (e.g., a blood pressure cuff). In some circumstances, blood pressure may be continuously, non-invasively monitored using multiple pulse oximetry sensors located at multiple body sites on a patient and calculating a differential pulse transit time (DPTT). However, blood pressure signals obtained by a blood pressure cuff or based on DPTT may be adversely affected by certain physiological events (e.g., changes in vasotone), and thus may not always accurately reflect the patient's blood pressure. Additionally, such blood pressure signals may be subject to other sources of error, such as improper placement of the blood pressure monitoring device or errors in processing the received data. Therefore, systems and methods for monitoring a patient's blood pressure and for determining a confidence level related to a blood pressure signal are provided herein.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

Figure 1:
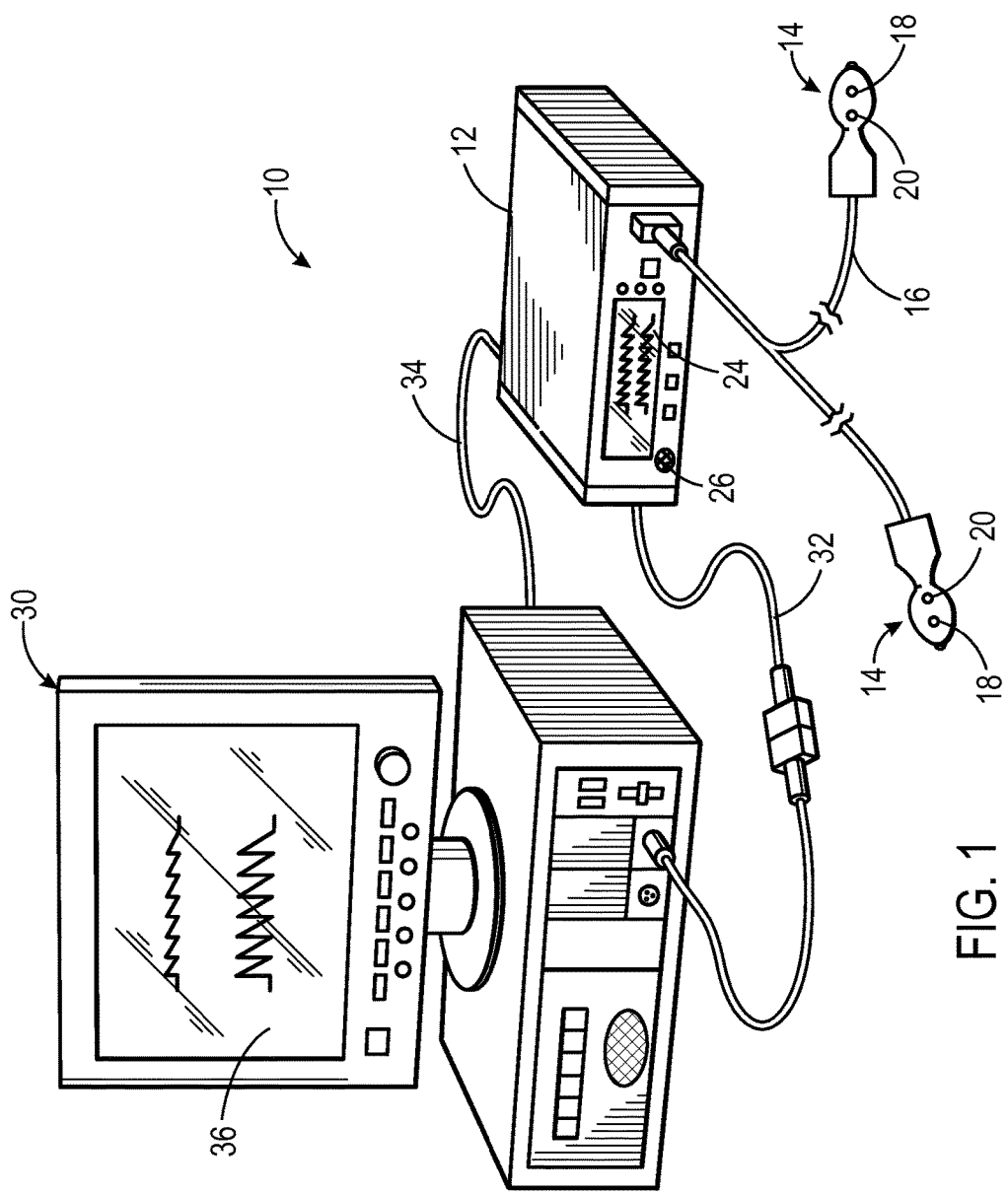
FIG. 1 is a perspective view of a medical monitoring system in accordance with an embodiment.

Provided herein are techniques for monitoring blood pressure and for determining a confidence level of the blood pressure signal. One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

A physician may monitor a patient's blood pressure through the use of various blood pressure monitoring devices and systems. For example, a patient's blood pressure may be monitored via a blood pressure cuff. In some cases, a patient's blood pressure may be derived by processing time delays between two or more characteristic points within a single plethysmography (PPG) signal obtained from a single pulse oximetry sensor. The characteristics points may be turning points of a derivative of the PPG signal or turning points of the PPG signal, for example. The time delay may correspond to the time it takes the pulse wave to travel a predetermined distance, such as a distance from the sensor to a reflection point and back to the sensor. Various techniques for deriving blood pressure based on a comparison of time delays between certain components of a single PPG signal obtained from a single sensor is described in U.S. Publication No. 2009/0326386, entitled "Systems and Methods for Non-Invasive Blood Pressure Monitoring," the entirety of which is incorporated herein by reference.

In other cases, a patient's blood pressure may be continuously, non-invasively monitored via multiple pulse oximetry sensors placed at multiple locations on the patient's body. As described in U.S. Pat. No. 6,599,251, entitled "Continuous Non-invasive Blood Pressure Monitoring Method and Apparatus" the entirety of which is incorporated herein by reference, multiple PPG signals may be obtained from the multiple pulse oximetry sensors, and the PPG signals may be compared against each other to estimate the patient's blood pressure. More particularly, when the locations of two sensors are at different distances from the patient's heart or along different paths (e.g., at the finger and forehead), a differential pulse transit time (DPTT) may be determined. The DPTT may then be used to compute blood pressure on a continuous or periodic basis (e.g., at predetermined intervals). A DPTT may represent the difference in arrival times of a portion of a cardiac wave between the two locations, and may be determined by comparing corresponding points in the two PPG signals. However, the DPTT may be adversely affected by various physiological events, such as changes in a patient's arterial compliance (e.g., vasotone). Additionally, the DPTT may be subject to various other sources of error, such as improper placement of the sensors or errors in processing the received data. Thus, the blood pressure signal derived from DPTT may not accurately reflect the patient's blood pressure. Blood pressure signals and measurements obtained via other blood pressure monitoring devices or techniques may also be subject to various sources of error.

In view of the foregoing, it may be desirable to determine a confidence level related to a blood pressure signal. Accordingly, provided herein are techniques for monitoring blood pressure and for determining a confidence level (e.g., a confidence measure, confidence metric, signal quality metric, quality metric, etc.) of the blood pressure signal (e.g., blood pressure measurement). The confidence level may relate to, and may provide some indication of, the accuracy and/or reliability of the blood pressure signal. Additionally, the confidence level may be provided to a caregiver or a user and/or certain actions may be triggered based on the determined confidence level. For example, the system may be configured to display a blood pressure signal and/or to provide a confirmation that the blood pressure signal is reliable if a blood pressure signal is determined to have a high confidence level. In some cases, the system may be configured to discard blood pressure data and/or to provide an alert if a blood pressure signal is determined to have a low confidence level. Such systems and methods may in turn provide improved patient monitoring and patient care.

In certain embodiments, the confidence level of the blood pressure signal may be determined based at least in part on a metric related to the PPG signal. In some embodiments, the metric may be a pulse shape metric. The pulse shape metric may be a center of area, a rotational moment, a mean, a median, a standard deviation, kurtosis, a pulse wave area, peak to peak amplitude, a mean path ratio, notch positioning, a natural frequency, a damping factor, or a skew, for example. The metrics may be determined with respect to the raw PPG signal or a derivative of the PPG signal (e.g., a first derivative, a second derivative, etc.). In certain embodiments, the metrics may be determined with respect to a whole pulse or only with respect to an upstroke portion (e.g., systolic) portion of the pulse. Additionally, in certain embodiments, the metrics may be determined with respect to an ensemble averaged derivative waveform with each pulse normalized in amplitude and/or in time using the pulse period prior to ensemble averaging. Each of the metrics may be expected to correlate with the blood pressure signal in a particular manner, and the relationship between the blood pressure signal and the pulse shape metric over a period of time may be used to determine a confidence level of the blood pressure signal. Additionally, any combination of two or more different pulse shape metrics may be used to determine a confidence level of the blood pressure signal. The present application generally describes a skew of a first derivative of a PPG signal (e.g., a skew metric) to facilitate explanation and to simplify discussion; however, as noted above, any suitable metric may be used in accordance with the disclosed techniques.

The skew metric trends with pulse pressure, and changes in the skew metric are expected to positively correlate with changes in blood pressure. Additionally, the skew metric may not be affected by changes in compliance of the arterial system (e.g., may be independent of changes in vasotone or compliance). Thus, a relationship or correlation between the change in the skew metric and the change in the blood pressure signal over a period of time may be utilized to determine the confidence level of the blood pressure signal, even during periods of changes in arterial compliance, as discussed in more detail below.

Additionally, the disclosed embodiments may be used to monitor a patient's blood pressure based on one or more pulse shape metrics, such as the skew of the PPG signal or the skew of the first derivative of the PPG signal. For example, the skew of the first derivative of the PPG signal may be appropriately scaled to provide a blood pressure signal. Such a system may facilitate blood pressure monitoring with fewer components (e.g., a single PPG sensor) and lower overall cost, thus improving the convenience of patient monitoring and lowering the cost of patient care.

With the foregoing in mind, FIG. 1 is a front perspective view of an embodiment of a medical monitoring system 10 that may be used for monitoring blood pressure and for determining a confidence level of the blood pressure signal. As shown, the system 10 includes a patient monitor 12 that is coupled to multiple sensors 14. The sensors 14 may be coupled to the monitor 12 wirelessly or via a cable 16. In one embodiment, the sensors 14 may be standard pulse oximetry sensors, and the monitor 12 may be a pulse oximetry monitor. Each of the sensors 14 may be configured to obtain a PPG signal, and the monitor 12 may be configured to process the PPG signals. As discussed in more detail below, in some embodiments, the system 10 may include only one sensor 14, multiple sensors 14, and/or may include additional types of sensors or monitoring devices (e.g., blood pressure monitoring devices).

Each sensor 14 may include one or more emitters 18 configured to transmit light. In addition, the sensor 14 may include one or more detectors 20 to detect light transmitted from the emitters 18 into a patient's tissue after the light has passed through the blood perfused tissue. The detectors 20 may generate a photoelectrical signal correlative to the amount of light detected. The emitter 18 and detector 20 may be disposed in a sensor housing. The emitter 18 may be a light emitting diode, a superluminescent light emitting diode, a laser diode or a vertical cavity surface emitting laser (VCSEL). Generally, the light passed through the tissue is selected to be of one or more wavelengths that are absorbed by the blood in an amount representative of the amount of the blood constituent present in the blood. The amount of light passed through the tissue varies in accordance with the changing amount of blood constituent and the related light absorption. For example, the light from the emitter 18 may be used to measure blood pressure, blood oxygen saturation, water fractions, hematocrit, or other physiological parameters of the patient. In certain embodiments, the emitter 18 may emit at least two (e.g., red and infrared) wavelengths of light. The red wavelength may be between about 600 nanometers (nm) and about 700 nm, and the IR wavelength may be between about 800 nm and about 1000 nm. However, any appropriate wavelength (e.g., green, yellow, etc.) and/or any number of wavelengths (e.g., three or more) may be used. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra, and that any suitable wavelength of light may be appropriate for use with the present disclosure.

The monitor 12 may be configured to receive and to process signals from one or more sensors 14. In certain embodiments, the monitor 12 may be configured to determine a patient's blood pressure based on the signals received from the sensors 14. For example, two sensors 14 may be positioned on the patient's body such the sensors 14 are located at difference distances from the patient's heart or along different paths from the patient's heart. The monitor 12 may be configured to determine the DPTT by comparing the difference in arrival times of a portion of a cardiac wave between the sensor locations, and the monitor 12 may be configured to derive the blood pressure signal based on the DPTT. As discussed above, the patient's blood pressure may also be derived from a single PPG signal obtained by a single sensor 14, in some embodiments.

Additionally or alternatively, the monitor 12 may be configured to determine various metrics based on the PPG signal. For example, the monitor 12 may be configured to determine a pulse shape metric, such as a skew of a first derivative (e.g., skew metric) of the PPG signal received from at least one sensor 14. As explained in more detail below, the monitor 12 may be configured to determine a confidence level of a blood pressure signal based at least in part on the skew metric. In certain embodiments, the monitor 12 may also be configured to determine various other physiological parameters, such as blood oxygen saturation, based on the signal received from the one or more sensors 14.

The monitor 12 may include a monitor display 24 configured to display information regarding the physiological parameters, information about the system, and/or alarm indications, for example. The monitor 12 may also include various input components 26, such as knobs, switches, keys and keypads, buttons, etc., to provide for operation and configuration of the monitor 12 and monitoring system 10. The monitor 12 may include a wireless module for transmitting and receiving wireless data, a memory, a processor, and various monitoring and control features.

As discussed above, the monitor 12 may determine blood pressure, the skew metric, and/or various physiological parameters of the patient. In certain embodiments the sensors 14, instead of or in addition to the monitor 12, may calculate the skew metric and/or various physiological parameters. In some embodiments, the monitor 12 may also be coupled to a multi-parameter monitor 30 via a cable 32 connected to a sensor input port or via a cable 34 connected to a digital communication port. In addition to the monitor 12, or alternatively, the multi-parameter monitor 30 may be configured to determine blood pressure, the skew metric, and/or various other physiological parameters. The multi-parameter monitor 30 may be configured to provide a central display 36 for visualization of information from the monitor 12 and from other monitoring devices or systems. The multi-parameter monitor 30 may facilitate presentation of patient data, such as blood pressure signals and/or confidence levels determined by system 10 and/or physiological parameters determined by the monitor 12 or by other patient monitoring systems (e.g., electrocardiographic (ECG) monitoring system, a respiration monitoring system, etc.). For example, the multi-parameter monitor 30 may display a graph of a blood pressure signal and a corresponding confidence level, a graph of SpO$_2$ values, a current pulse rate, an electrocardiograph, and/or other related patient data in a centralized location for quick reference by a medical professional. Although cables 32 and 34 are illustrated, it should be understood that the monitor 12 may be in wireless communication with the multi-parameter monitor 30.

If in wireless communication, the various wireless transceivers/receivers of the various components of the system 10, may be configured to communicate using the IEEE 802.15.4 standard, and may be, for example, ZigBee, WirelessHART, or MiWi modules. Additionally or alternatively, the wireless modules may be configured to communicate using the Bluetooth standard, one or more of the IEEE 802.11 standards, an ultra-wideband (UWB) standard, or a near-field communication (NFC) standard. As described further below, the PPG sensor 14 may wirelessly transmit either raw detector signals or calculated physiological parameter values to the patient monitor 12. Additionally, the monitor 12 may use the wireless module to send the sensor 14 instructions and/or operational parameters set by a user or an operator using the monitor 12.

The multiple sensors 14 illustrated in FIG. 1 may be utilized to determine the DPTT for continuous non-invasive blood pressure monitoring. However, it should be understood that the system 10 may have only a single sensor 14 and may be configured to determine the blood pressure signal, the skew metric, and/or the confidence level using only a single sensor 14. Thus, the blood pressure signal may be determined from the PPG signal from the single sensor 14. For example, in some embodiments, the blood pressure measurements may be derived by processing time delays between characteristic points of a single PPG signal obtained from the single sensor 14, and the skew metric may also be derived based on the single PPG signal obtained from the single sensor 14. Alternatively, or in addition, it should be understood that the blood pressure signal may be obtained through any suitable blood pressure monitoring device or techniques. In such systems, the blood pressure monitoring device may obtain a blood pressure signal and provide the blood pressure signal to the monitor 12 or to the multi-parameter monitor 30, for example. The blood pressure monitoring device may communicate the blood pressure signal to the monitor 12 or to the multi-parameter monitor 30 wirelessly or via a cable, for example. The monitor 12 or multi-parameter monitor 30 may receive the blood pressure signal and may determine a confidence level of the blood pressure signal based at least in part on the skew metric. In such systems, only a single sensor 14 may be required to derive the skew metric for determining the confidence level of the blood pressure signal.

Figure 2:
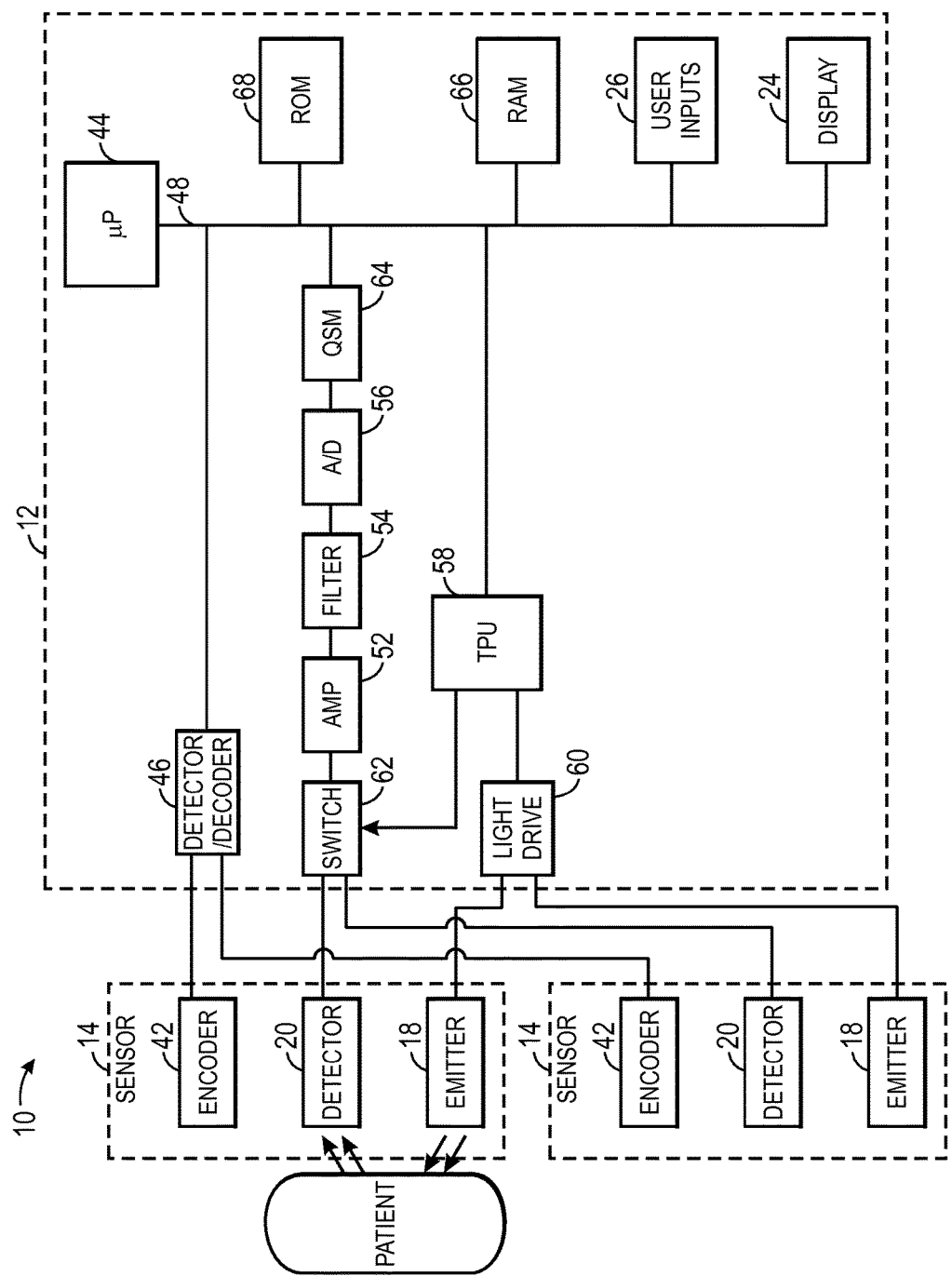
FIG. 2 is a block diagram of the medical monitoring system of FIG. 1, in accordance with an embodiment.

FIG. 2 is a block diagram of the system 10. As discussed above, the sensors 14 may include one or more emitters 18 capable of emitting one or more wavelengths of light, and one or more detectors 20 capable of detecting light at various intensities and wavelengths. In such embodiments, the data provided by the sensors 14 may be used to calculate physiological parameters, such as blood pressure, blood oxygen saturation, and pulse rate. Additionally, the PPG signal may be used by the monitor 12 to calculate the skew metric. The skew metric may in turn be utilized to determine the confidence level of the blood pressure signal, as described in more detail below. Again, although multiple sensors 14 are shown in FIG. 2, it should be understood that the second sensor is optional, and only a single sensor 14 may be used in some embodiments.

In operation, light enters the detector 20 after propagating through the tissue of the patient. The detector 20 may convert the light at a given intensity, which may be directly related to the absorbance and/or reflectance of light in the tissue of the patient, into an electrical signal. Each sensor 14 may also include an encoder 42, which may contain information about the sensor 14, such as what type of sensor it is (e.g., a type of sensor, a location where the sensor is to be placed, etc.) and how the sensor 14 is to be driven (e.g., wavelength of light emitted by the emitter 18). This information may allow the monitor 12 to select appropriate algorithms and/or calibration coefficients or to derive a filter for estimating the patient's physiological characteristics.

The encoder 42 may, for instance, be a memory on which information may be stored for communication to the monitor 12. The encoder 42 may store information related to the wavelength of the emitters 18. The encoder 42 may, for instance, be a coded resistor, EEPROM or other coding devices (such as a capacitor, inductor, PROM, RFID, parallel resident currents, or a colorimetric indicator) that may provide a signal to a microprocessor 44 or other processing circuitry of the monitor 12 related to the characteristics of the sensor 14 to enable the microprocessor 44 to determine the appropriate calibration characteristics. In some embodiments, the data or signal from the encoder 42 may be decoded by a detector/decoder 46 in the monitor 12. In some embodiments, the encoder 42 and/or the decoder 46 may not be present.

The microprocessor 44 of the monitor 12 may be coupled to an internal bus 48. The received signal from the sensor 14 may be passed through an amplifier 52, a low pass or bandpass filter 54, and an analog-to-digital converter 56. A time processing unit (TPU) 58 may provide timing control signals to light drive circuitry 60, which controls when the optical components of the optical sensor (e.g., sensor 14) is activated, and, if multiple light sources are used, the multiplexed timing for the different light sources. TPU 58 may also control the gating-in of signals from sensor 14 or sensors 14 through a switching circuit 62. These signals are sampled at the proper time, depending at least in part upon which of multiple light sources is activated, if multiple light sources are used. The digital data may then be stored in a queued serial module (QSM) 64, for later downloading to RAM 66 or ROM 68 as QSM 64 fills up. In addition, the monitor 12 may include a display 24 and control inputs 26, such as knobs, switches, keys and keypads, touchscreens, buttons, etc., to provide for operation and configuration of the monitor 12.

Based at least in part upon the received signals corresponding to the light received by optical components of the sensors 14, the microprocessor 44 may determine the skew metric, the blood pressure, the oxygen saturation, the heart rate, and/or other physiological parameters using various algorithms. The algorithms may employ certain coefficients, which may be empirically determined, and may correspond to the wavelengths of light used. The algorithms and coefficients may be stored in a ROM 68 or other suitable computer-readable storage medium or memory circuitry and accessed and operated according to microprocessor 44 instructions. Additionally, the microprocessor 44 may determine the confidence level of the blood pressure signal based on the skew metric.

As discussed above, one or more functions of the monitor 12 may also be implemented directly in the sensors 14. For example, in some embodiments, the sensors 14 may include one or more processing components configured to calculate the skew metric, the blood pressure, the confidence level, and/or various physiological parameters from the signals obtained from the patient. The sensors 14 may have varying levels of processing power, and may wirelessly output data in various stages to the monitor 12. For example, in some embodiments, the data output to the monitor 12 may be analog signals, such as detected light signals (e.g., pulse oximetry signals or regional saturation signals), or processed data.

Figure 3A:
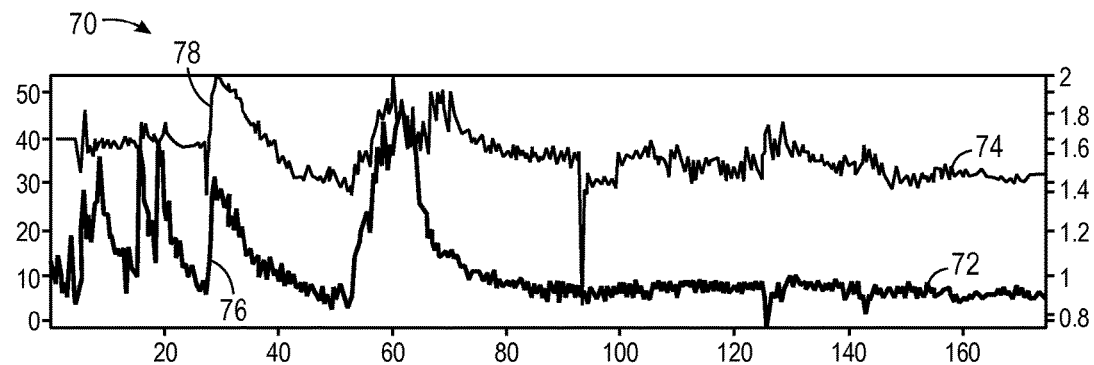
FIG. 3A illustrates an example of a skew of a first derivative of a plethysmography signal and a pulse pressure signal over a period of time.
Figure 3B:
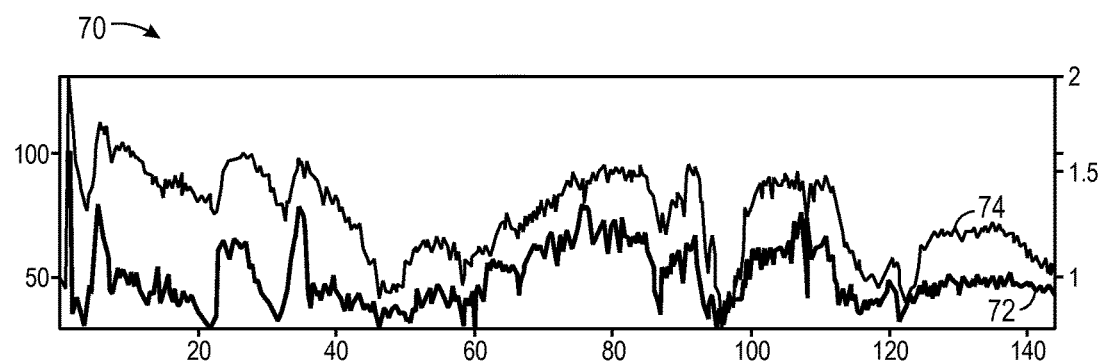
FIG. 3B illustrates another example of a skew of a first derivative of a plethysmography signal and a pulse pressure signal over a period of time.
Figure 3C:
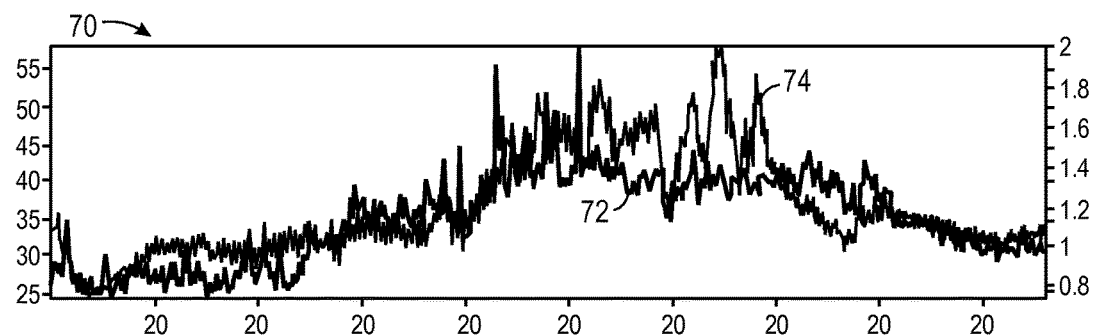
FIG. 3C illustrates another example of a skew of a first derivative of a plethysmography signal and a pulse pressure signal over a period of time.

According to various embodiments, the system 10 may be utilized to determine the confidence level of the blood pressure signal. As indicated above, the confidence level may be based at least in part on a pulse shape metric, such as a skew metric. FIGS. 3A-3C depicts examples of the skew metric 72 and the pulse pressure 74 over a period of time. The skew metric 72 was determined from a PPG signal obtained from the patient, as explained in more detail below. The pulse pressure 74 was measured via a peripheral arterial line placed in an arm of the patient. Pulse pressure is the difference between systolic pressure and diastolic pressure, and is related to a patient's blood pressure. As shown in FIGS. 3A-3C, the skew metric generally trends with the pulse pressure. Thus, the skew metric is also expected to generally positively correlate with (e.g., trend with) the blood pressure signal. With reference to FIG. 3A, an increase 76 in the skew metric 72 attends an increase 78 in the pulse pressure 74. In the illustrated example, a drug (e.g., a vasoactive drug) was administered to the patient just prior to the increase 78 in pulse pressure 74. As shown, the skew metric 72 trended with the increasing pulse pressure 74 even after administration of the drug (e.g., the skew metric 72 was not adversely affected by administration of the drug or by changes in arterial compliance due to the drug). Accordingly, a relationship or correlation between the skew metric 72 and the blood pressure signal over a period of time can be used to determine the confidence level of the blood pressure signal, even in the presence of changes in arterial compliance and changes in vasotone.

Skew metrics generally measure the asymmetry of a signal around a mean or average value, and thus generally characterize the degree of asymmetry and the shape of such signals. The monitor 12 may be configured to derive and analyze the skew metric from the PPG signal via any suitable method. For example, the monitor 12 may identify individual pulses and then derive and analyze the skew metric from each individual pulse. One or more digital IR and red waveforms may be bandpassed, normalized, and whitened to produce one or more filtered waveforms. These filtered waveforms may then be used to calculate the skew metric. In an embodiment, components of the skew metric may be calculated as follows:

$$\text{skew} = \frac{n \cdot \sum_t (x_t - \bar{x})^3}{((n-1)(n-2)(\sigma^3))} \text{ where } x_t = (PPG_t - PPG_{t-1})$$

The skew metric may be monitored continuously over time and/or the skew metric may be determined periodically for a particular period of time (e.g., 30 seconds, 1 minute, 2 minutes, etc.). In an embodiment, the skew metric is determined continuously as a moving average over a time window (e.g., 30 seconds, 1 minute, 2 minutes, etc.).

As discussed in more detail below, the skew metric can be utilized to determine the confidence level of the blood pressure signal. The skew metric is not adversely affected by changes in vasotone, and the skew metric trends with the patient's blood pressure even during periods of change in vasotone. Thus, the skew metric is particularly well-suited for providing a validation and for determining a confidence level of blood pressure signals, such as a blood pressure signal derived from DPTT, derived from a single PPG waveform, or received from a blood pressure monitoring device. For example, if the blood pressure signal does not trend with the skew metric, it may indicate that the blood pressure signal is adversely affected by changes in vasotone or that the measurement was subject to some other source of error. Various methods for monitoring blood pressure and for determining the confidence level of the blood pressure signal are discussed in more detail below.

FIGS. 4-8 are flow charts illustrating various methods for monitoring blood pressure, in accordance with the present disclosure. The methods include various steps represented by blocks. It should be noted any of the methods provided herein, may be performed as an automated procedure by a system, such as system 10. Although the flow charts illustrate the steps in a certain sequence, it should be understood that the steps may be performed in any suitable order and certain steps may be carried out simultaneously, where appropriate. Further, certain steps or portions of the methods may be performed by separate devices. For example, a first portion of the method may be performed by a blood pressure monitoring device, while a second portion of the method may be performed by the sensor 14 and/or monitor 12. In addition, insofar as steps of the methods disclosed herein are applied to the received signals, it should be understood that the received signals may be raw signals or processed signals. That is, the methods may be applied to an output of the received signals.

Figure 4:
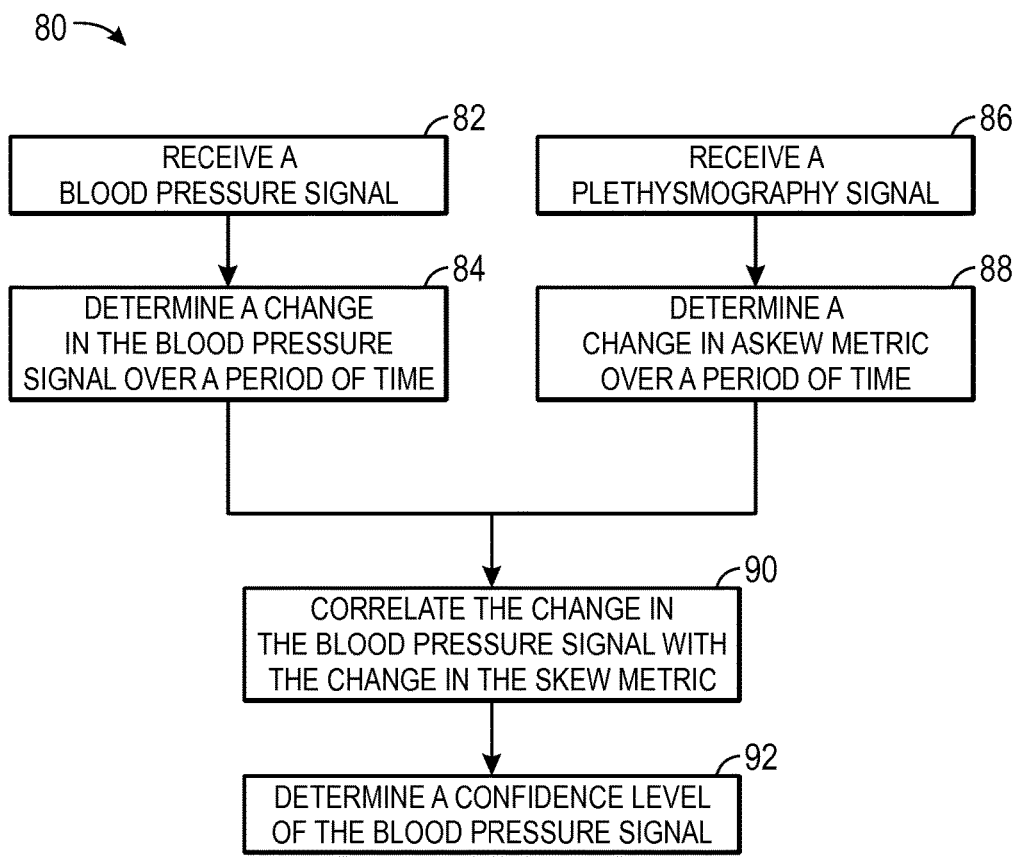
FIG. 4 is a process flow diagram of a method of monitoring blood pressure, in accordance with an embodiment.

With reference to FIG. 4, a method for monitoring blood pressure according to an embodiment is generally indicated by reference number 80. In certain embodiments, the method 80 begins with receiving a blood pressure signal at step 82. The blood pressure signal may be received from any suitable blood pressure monitoring device. In certain embodiments, the blood pressure signal may be derived from one or more PPG signals obtained by one or more sensors 14. For example, the blood pressure signal may be derived from the DPTT derived from the PPG signals from two sensors 14. Alternatively, the blood pressure signal may be derived from the PPG signal of a single sensor 14. At step 84, a monitoring device, such as the monitor 12, may determine a change in the blood pressure signal over a period of time. At step 86, a PPG signal may also be received by the monitor 12. In certain embodiments, the PPG signal may be obtained by the one or more sensors 14. At step 88, the monitor 12 may determine the change in the skew metric of the PPG over the period of time.

As discussed above, the skew metric trends with blood pressure. Thus, it is expected that positive changes in the skew metric will attend positive changes in the blood pressure signal. Similarly, it is expected that negative changes in the skew metric will attend negative changes in the blood pressure signal. Thus, at step 90, the monitor 12 may be configured to correlate the change in the skew metric and the change in blood pressure signal over the period of time. At step 92, the monitor 12 may be configured to determine a confidence level of the blood pressure signal based at least in part on the correlation between the change in the skew metric and the change in the blood pressure signal over the period of time.

Figure 5:
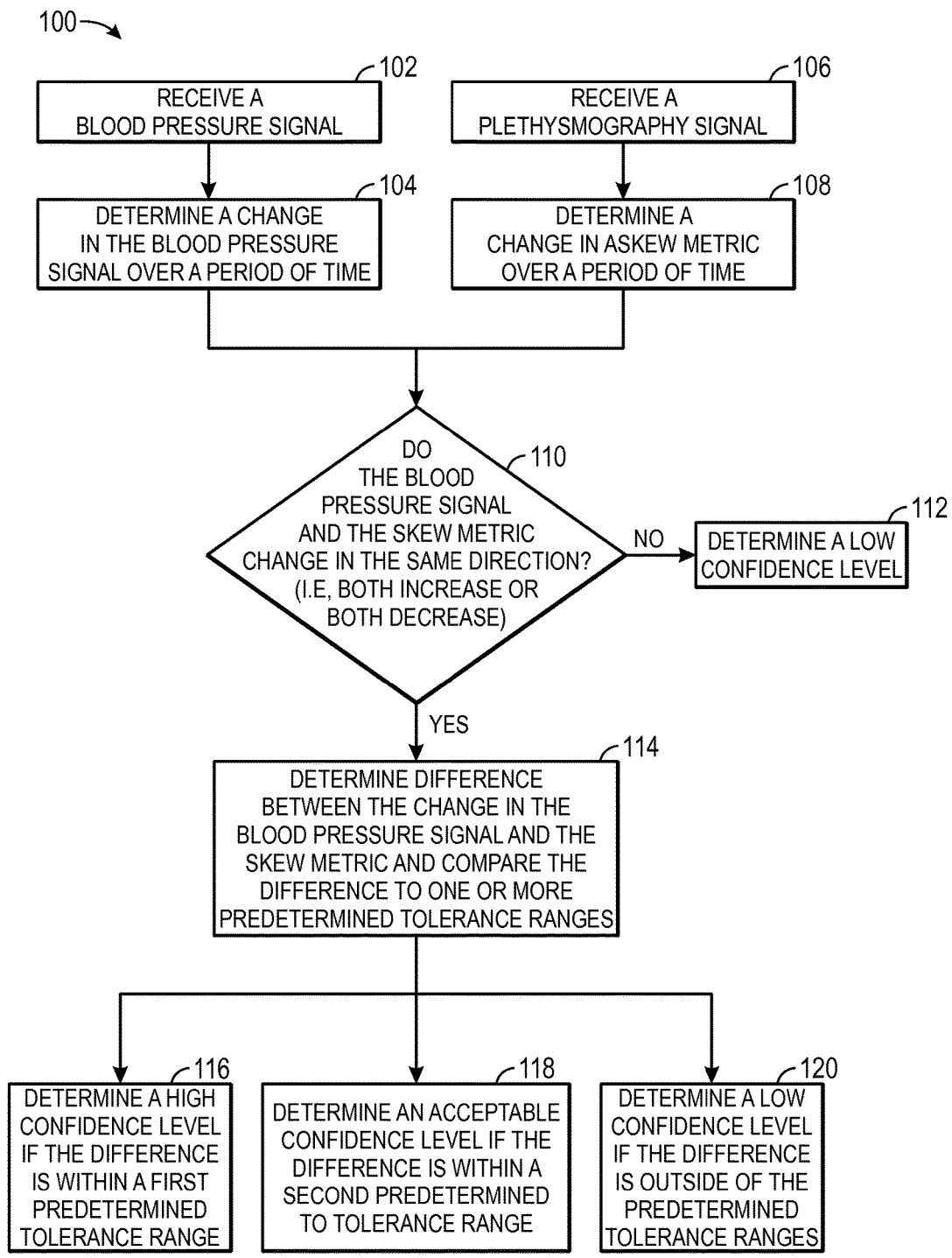
FIG. 5 is a process flow diagram of a method of monitoring blood pressure, in accordance with an embodiment.

FIG. 5 is a process flow diagram illustrating another method for monitoring blood pressure, in accordance with an embodiment. The method is generally indicated by reference number 100. As in FIG. 4, the method 100 also begins with receiving a blood pressure signal at step 102. At step 104, the monitor 12, may determine a change in the blood pressure signal over a period of time. At step 106, a PPG signal may also be received by the monitor 12, and at step 108, the monitor 12 may determine a change in the skew metric over the period of time at step 108.

Block 110 generally relates to one technique for correlating the change in the blood pressure signal to the change in the skew metric. As shown at step 110, correlating the change in the blood pressure signal with the change in the skew metric may include determining whether the blood pressure signal and the skew metric change in the same direction (e.g., trend in the same direction, positively correlate, both increase, or both decrease, etc.) over the period of time. As indicated above, the blood pressure signal and the skew metric are expected to change in the same direction if the monitoring system is functioning properly and if the blood pressure signal accurately reflects the patient's blood pressure.

In certain embodiments, if the blood pressure signal and the skew metric do not change in the same direction, a low confidence level may be determined, as in step 112. The low confidence level may indicate that the blood pressure signal is not reliable or that the blood pressure signal may not accurately reflect the condition of the patient. For example, the patient may be experiencing changes in vasotone that adversely affect the blood pressure signal or the sensor 14 may not be accurately positioned on the patient. Additionally, certain suitable actions may be trigged when the low confidence level is determined. For example, in some embodiments, the blood pressure signal may be discarded (e.g., blood pressure data from the period of time is not used) and/or the blood pressure signal (or parameters related to the blood pressure) may not be provided to the user or the caregiver. In some embodiments, an indication of the low confidence level may be provided to the user or the caregiver, along with the blood pressure signal. The indication of the low confidence level may include a visual or audible indicator, such as a message or signal on the display of the monitor 12 or an audible alarm, for example. Furthermore, in certain embodiments, the monitor 12 may be configured to initiate another blood pressure measurement or may prompt the user to initiate another blood pressure measurement if the low confidence level is determined.

However, as shown in FIG. 5, if the blood pressure signal and the skew metric are determined to change in the same direction at step 110, the method 100 may proceed to step 114. Step 114 also generally relates to one technique for correlating the change in the blood pressure signal to the change in the skew metric. As shown in step 114, correlating the change in the blood pressure signal with the change in the skew metric may include determining a difference between the change in the blood pressure signal and the change in the skew metric, and comparing the difference to one or more predetermined (e.g., predefined, programmed, stored, user defined, etc.) tolerance ranges. In addition to trending with the blood pressure signal, the skew metric and the blood pressure signal are also expected to change in a similar manner (e.g., similar percent change) over the period of time if the system is functioning properly and if the blood pressure signal accurately reflects the patient's blood pressure. Thus, gradations of confidence (e.g., multiple confidence levels) may be determined based on the degree with which the skew metric and the blood pressure signal correlated over the period of time.

Thus, in some embodiments, the system may determine a high confidence level if the difference is within a first predetermined tolerance range, as shown in step 116. The first predetermined tolerance range may be reasonably narrow to ensure that only reasonably reliable blood pressure signals are determined at the high confidence level. For example, if there is a difference of less than 1% (e.g., between 0 and 1%), 2%, 3%, 4%, 5%, 6%, 7%, 8%, 9%, 10% or any suitable amount, between the amplitude changes of the two signals, then the high confidence level may be assigned. The high confidence level may indicate that the blood pressure signal is reliable or that the blood pressure signal is expected to accurately reflect the condition of the patient. Certain suitable actions may be triggered if a high confidence level is determined. In some embodiments, the blood pressure signal may be provided to the user or the caregiver. The blood pressure signal may be provided on the display 24 of the monitor 12, for example. Additionally, in some embodiments, an indication of the high confidence level may be provided to the caregiver or the user. The indication may be a visual or an audible indicator, such as a message or a signal provided via the display 14 of the monitor 12.

In some embodiments, the system may determine a second confidence level, such as an acceptable or medium confidence level, if the difference is within a second predetermined tolerance range, as shown in step 118. The second predetermined tolerance range should be reasonably narrow so as to ensure that only acceptably reliable blood pressure signals are determined to have the acceptable confidence level. For example, if the difference between the change in the skew metric and the change in the blood pressure signal over the period of time is within about 5-10%, 5-10%, 10-20%, 15-20%, or within any suitable range, then the system may determine an acceptable confidence level. The second predetermined tolerance range may depend in part on the first predetermined tolerance range and may be generally larger than the first predetermined range (e.g., may encompass relatively larger differences between the change in the blood pressure signal and the change in the skew metric). The acceptable confidence level may indicate that the blood pressure signal is acceptably reliable or that the blood pressure signal may acceptably reflect the condition of the patient.

Additionally, certain suitable actions may be triggered if an acceptable confidence level is determined. For example, in some embodiments, the blood pressure signal may be provided to the user or the caregiver. However, in certain embodiments, the blood pressure signal may be discarded and/or may not be displayed. In some embodiments, the user may provide a user input to control whether the blood pressure signal is to be provided in the event that an acceptable confidence level is determined. For example, prior to a monitoring session, the user may provide an input based on the user's preferences, the patient's condition, or the like. In some embodiments, an indication of the acceptable confidence level may be provided to the caregiver or the user. The indication may be a visual or audible indicator, such as a message or signal (e.g., an alarm) provided via the display 16 of the monitor 12. Additionally, the acceptable confidence may be utilized in alarming systems to reduce the incidence of false alarms and/or to provide more information related to alarms, as discussed above.

As shown in step 120 of FIG. 5, the system may determine a low confidence level if the blood pressure signal and the skew metric change in the same direction (as determined at step 110), but the difference between the change in the blood pressure signal and the change in the skew metric is outside of the predetermined tolerance ranges (e.g., the first and the second predetermined tolerance ranges, or other suitable predetermined tolerance range). Such a method facilitates identification of unreliable blood pressure signals if the change in the skew metric does not trend with the change in the blood pressure signal in a similar manner or degree. A large difference between the change in the skew metric and the change in the blood pressure signal over the period of time may indicate that the blood pressure signal is not accurate or reliable. By way of example, the monitor 12 may be configured to determine the high confidence level if the difference between the change in the blood pressure signal and the change in the skew metric over the period of time is less than 5%, an acceptable confidence level if the difference is more than 5% but less than 20%, and a low confidence level if the difference is greater than 20%. Thus, if the blood pressure signal increases by 30% over the period of time, but the skew metric only increases by 5%, or, for example, if the blood pressure signal increases 30% more than the skew metric increases, then a low confidence level may be determined in step 120. In such cases, certain suitable actions may be triggered by the determination of the low confidence level, as set forth above.

It should be understood that the various predetermined tolerance ranges provided above are examples only and are not intended to be limiting. Indeed, any suitable tolerance ranges and any number of tolerance ranges (e.g., 2, 3, 4, 5, 6, 7, 8, or more tolerance ranges) may be utilized to establish various confidence levels. In such cases, suitable notifications may be provided and appropriate actions may be triggered based on the determined confidence level, including the actions set forth above. Additionally, the predetermined tolerance ranges may be programmed into the sensor 14 and/or the monitor 12 at manufacture, or alternatively, the predetermined tolerance ranges may be programmed or selected by the user. For example, the user may set predetermined tolerance ranges based on the user's preferences, the patient's condition, or the like. The user may change the tolerance ranges over the course of monitoring a patient, based on the patient's history or condition. In an embodiment, the sensor 14 and/or monitor 12 may be programmed to automatically change the tolerance ranges based on certain identified patient conditions or data patterns.

As noted above, it should be understood that the steps of FIG. 4 and FIG. 5 may be carried out in any suitable order or sequence and the steps of the methods may be adapted and adjusted to accommodate system and patient requirements. For example, in some embodiments, the blood pressure signal and the PPG signal may be received and/or processed simultaneously (e.g., the change in blood pressure and the change in the skew metric may be determined simultaneously). Additionally, in the method 100 of FIG. 5, the difference between the change in the blood pressure signal and the change in the skew metric (step 114) may be determined prior to determining whether the blood pressure and the skew metric change in the same direction (step 110), or vice versa. In some embodiments, certain steps shown in FIG. 5 may be omitted to increase processing speed or to provide flexibility in the method. For example, the method may not include determining the difference, but may determine a low confidence level (step 112) if the blood pressure signal and the skew metric change in the opposite direction (step 110), and a high confidence level if the blood pressure signal and the skew metric change in the same direction.

Additionally, the determination of a confidence level in accordance with FIG. 4 and FIG. 5 may provide additional utility in certain blood pressure monitoring systems. Some blood pressure monitoring systems may be configured to provide an alarm when large or clinically significant changes in blood pressure are detected within a period of time or when the blood pressure signal is outside of a certain range. For example, the system may be configured to provide an alarm if the blood pressure signal indicates that the patient's blood pressure has changed by a clinically significant amount (e.g., about 20 mmHg/minute, in some embodiments). In such systems, the determination of the confidence level may be utilized to reduce the incidence of false alarms and/or to validate the alarm. For example, if the low confidence level is determined, the alarm may be disabled and the blood pressure monitoring system may not output or may delay the alarm, thus reducing the incidence of false alarms. The determination of the high confidence may be utilized to validate alarms related to blood pressure measurements (e.g., clinically high blood pressure) and to improve the accuracy and reliability of such alarming methods in blood pressure monitoring. For example, the blood pressure monitoring system may be configured to only output the alarm if the signal is associated with a high or acceptable confidence level. In some embodiments, the system may provide an indication of the confidence level along with the alarm.

Figure 6:
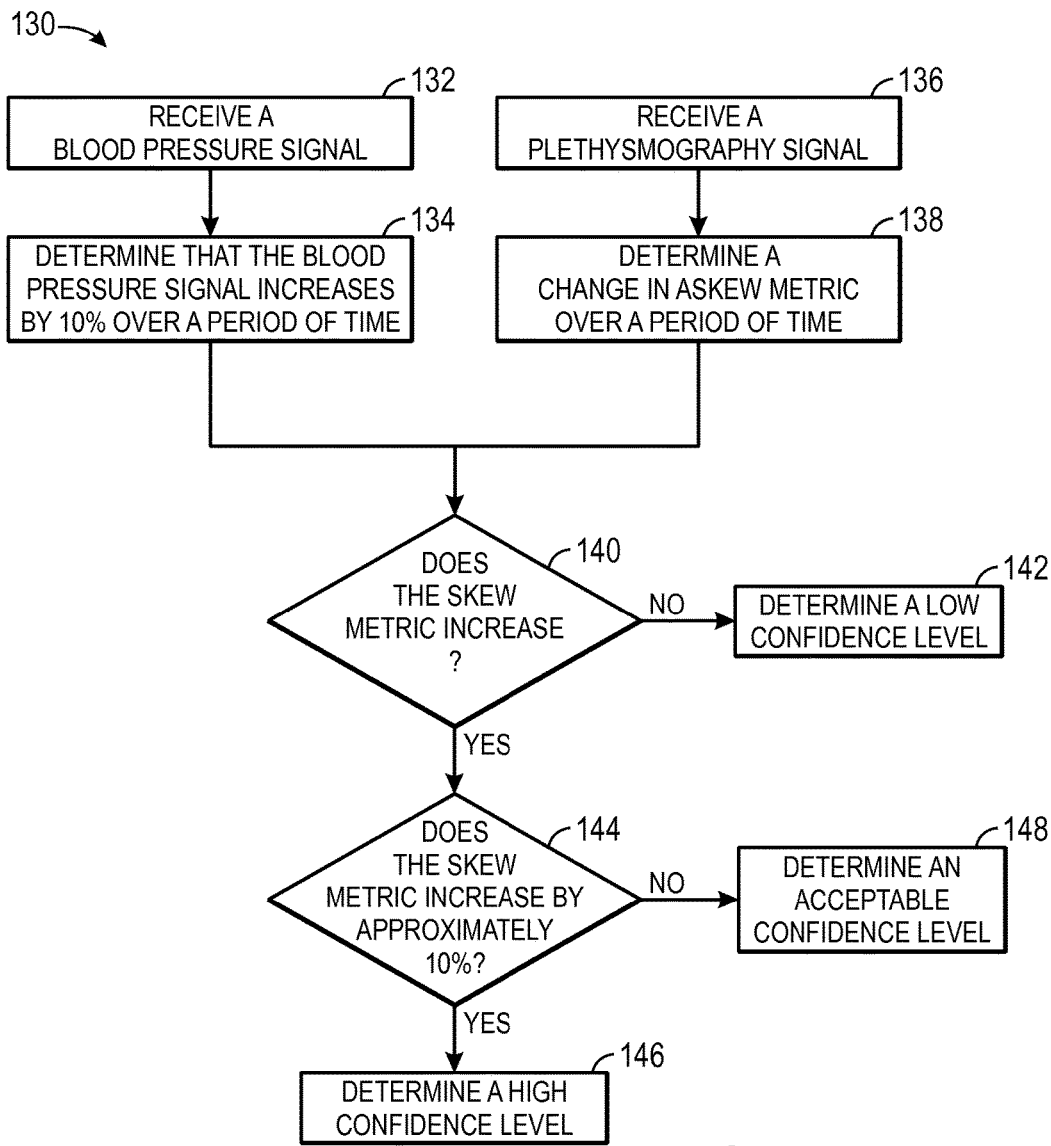
FIG. 6 is a process flow diagram of an implementation of a method of monitoring blood pressure, in accordance with an embodiment.

FIG. 6 is an example of an implementation of a method for monitoring blood pressure, in accordance with an embodiment of the present disclosure. The method is generally indicated by reference number 130. As shown in this implementation, a blood pressure signal is received at step 132 and a percentage change in the blood pressure signal over a period of time is determined at step 134. In this example, the blood pressure signal increases by about 10% over the period of time, although it should be understood that in practice the blood pressure signal may increase or decrease by any percentage (e.g., 5%, 15%, 20%, 25%, etc.). At step 136, a PPG signal is received, and a change in a skew metric over the period of time is determined at step 138. At step 140, the system may determine whether the skew metric changes in the same direction as the blood pressure signal. For example, where the blood pressure signal increased by 10%, the system determines if the skew metric also increased. If the skew metric does not change in the same direction as the blood pressure signal, then a low confidence level may be determined and appropriate actions may be triggered at step 142. In some embodiments, if the skew metric changes in the same direction as the blood pressure signal, the system may then determine whether the skew metric changes by approximately the same percentage at step 144. For example, the system may determine if the skew metric also increased by about 10%. If the skew metric increases by approximately the same percentage (for example, also increased by 10%), or within a tolerance range of that percentage (for example, plus or minus about 2 percentage points, or within 8 to 12%), then the system may determine a high confidence level at step 146, and appropriate actions may be triggered. If the change in the skew metric is outside of the first predetermined tolerance of the percentage change in blood pressure (and, optionally, within a second tolerance range), then the system may determine an acceptable confidence level of the blood pressure signal at step 148, and appropriate actions may be triggered. For example, in the example provided, if the change in the skew metric is not approximately 10%, the system may determine the acceptable confidence level. Additionally, if the change in the skew metric is outside of the second tolerance of the change in blood pressure, then a low confidence level may be indicated. As indicated above, the steps of the method may be carried out in any suitable sequence, and any suitable tolerance ranges and any number of tolerance ranges may be utilized to determine various confidence levels.

In some embodiments, certain steps of the methods set forth in FIGS. 4-6 may not be carried out unless or until the system detects a blood pressure signal that changes by a certain amount or percentage over a period of time. For example, in the example of FIG. 6, the system may be configured to initiate the determination of the skew metric and/or the confidence level only if the blood pressure signal changes by 10% or more over a period of time. Thus, the blood pressure may be continuously monitored without determining confidence levels of the signal, and the skew metric and the confidence level are only determined if the blood pressure signal changes by a certain threshold amount, or if a predetermined time interval has passed. In some embodiments, the system may be configured to switch from periodically (e.g., at predefined intervals) validating the blood pressure signal based on the skew metric to continuously evaluating the reliability of the blood pressure signal based on the skew metric if large changes in the blood pressure signal are detected. Such systems may reduce processing steps and improve processing speed, but may still provide a check or indication of confidence levels during periods of large changes in the blood pressure signal.

Figure 7:
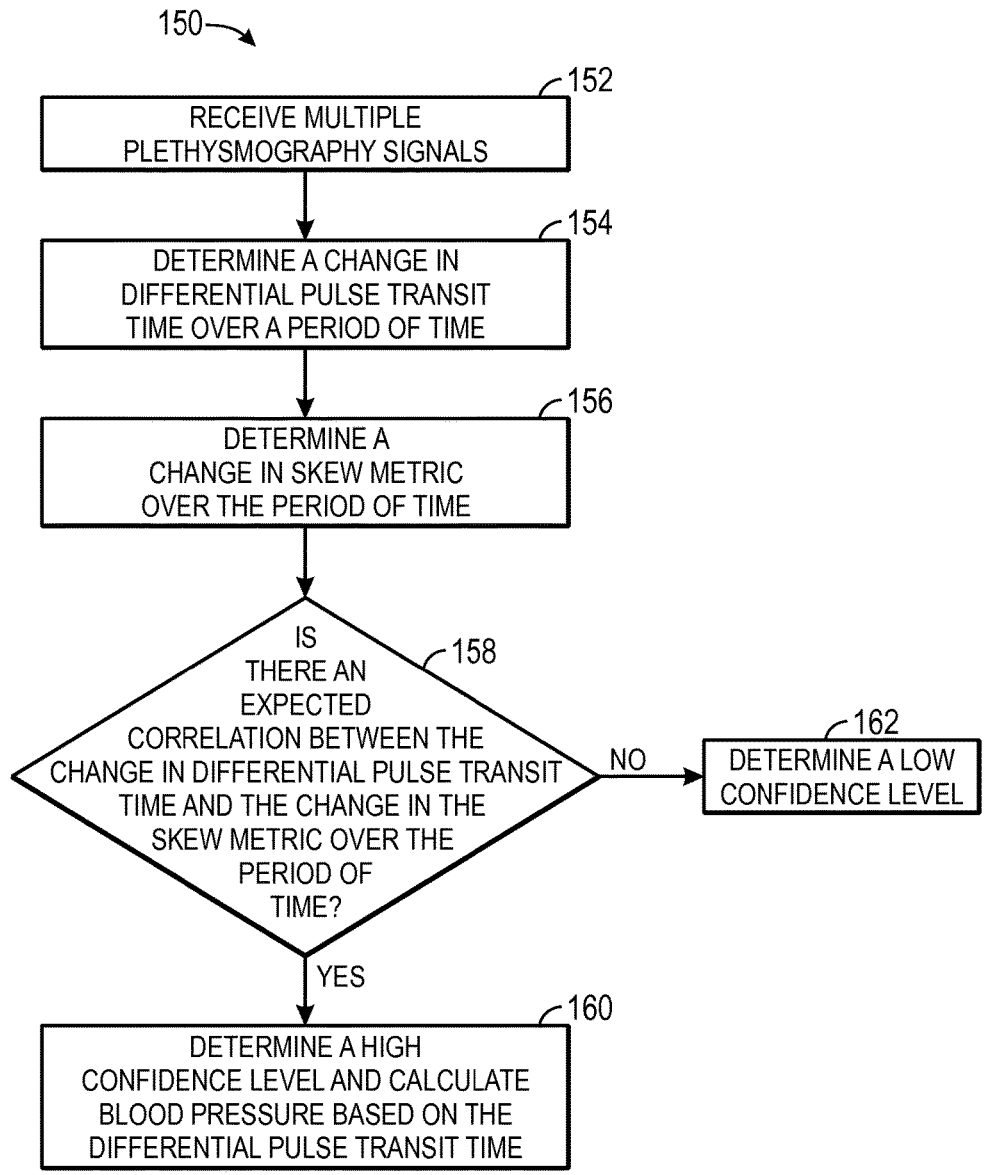
FIG. 7 is a process flow diagram of a method of monitoring blood pressure based on a differential pulse transit time, in accordance with an embodiment.

FIG. 7 is a process flow diagram illustrating another method for monitoring blood pressure, in accordance with one embodiment. As discussed above, in some embodiments, blood pressure may be continuously, non-invasively monitored based on the DPTT. As noted above, the DPTT may be obtained by using multiple sensors 14 located at multiple sites on a patient. The multiple PPG signals obtained from the multiple sensors 14 may be compared against each other to determine DPTT and from that estimate the patient's blood pressure. However, the DPTT may be adversely affected by various physiological events and conditions, such as changes in vasotone. Thus, the DPTT may not always provide accurate estimations of the blood pressure of the patient. In some embodiments, it may be desirable to determine a confidence level related to the DPTT, which may provide an indication of whether the DPTT can be reliably used to monitor blood pressure.

The DPTT trends negatively with blood pressure, and thus, the DPTT is expected to trend negatively with the skew metric. This inverse correlation or relationship may be utilized by the system 10 to determine whether the DPTT can be reliably used to monitor blood pressure. The determination may be made via similar methods as set forth in FIGS. 4-7, although the methods should be adapted to account for the fact that the DPTT is expected to negatively correlate with the skew metric. Determining the confidence level in the DPTT may eliminate unnecessary processing steps and improve the processing speed of certain blood pressure monitoring systems. For example, if the expected correlation is not present between the DPTT and the skew metric, the DPTT data may be discarded without unnecessarily calculating an inaccurate or unreliable blood pressure signal.

As illustrated in method 150 of FIG. 7, multiple PPG signals are received at step 152. At step 154, the change in the DPTT is determined over a period of time. At step 156, the change in the skew metric is also determined over the period of time based on at least one of the received PPG signals. At step 158, the monitor 12 may determine whether there is an expected correlation between the change in the DPTT and the change in the skew metric. As indicated above, it is expected that decreases in the skew metric will attend increases in the DPTT. Similarly, it is expected that increases in the skew metric will attend decreases in the DPTT. If the expected correlation is present, the system may determine a high confidence level in the DPTT at step 160, and certain suitable actions may be triggered. For example, in some embodiments, the monitor 12 may proceed to calculate blood pressure based on the DPTT. In certain embodiments, the monitor 12 may provide an indication of the high confidence level to the user or the caregiver, as set forth above. However, if the expected correlation is not present, the system may determine a low confidence level in the DPTT at step 162, and certain suitable actions may be triggered. For example, in some embodiments, the DPTT data may be discarded and/or the monitor 12 may not proceed to derive the blood pressure from the DPTT data. In certain embodiments, an indication of the low confidence level may be provided, as set forth above. It should be understood that the method 150 may be adapted to determine gradations in confidence levels as described above with respect to FIG. 5. For example, in some embodiments, the method 150 may be adapted to determine whether the DPTT and the skew metric change in the same direction and/or to determine whether the difference between the change in the DPTT and the change in the skew metric is within one or more predetermined tolerance ranges as described above with respect to FIG. 5.

As noted above, any of a variety of other suitable metrics may be used to determine the confidence level of a blood pressure signal in accordance with the techniques disclosed herein. For example, in some embodiments, the metric may be any suitable pulse shape metric. The pulse shape metric may be a center of area, a rotational moment, a mean, a median, a standard deviation, kurtosis, a pulse wave area, peak to peak amplitude, a natural frequency, or a damping factor. Additionally, in some embodiments, an indirect pulse shape metric may be utilized to determine the confidence level of the blood pressure signal. By way of example, a first Gaussian function may be fitted to a first peak of the blood pressure signal, and successive Gaussian functions may be iteratively fitted to subsequent residuals. A position and an amplitude of these fitted Gaussian functions may provide an indirect metric that describes the shape of the blood pressure signal.

As noted above, the metrics may be determined with respect to the raw PPG signal or a derivative of the PPG signal (e.g., a first derivative, a second derivative, etc.). In certain embodiments, the metrics may be determined with respect to a whole pulse or only with respect to an upstroke portion (e.g., systolic) portion of the pulse. Each of the metrics may be expected to correlate with the blood pressure signal in a particular manner, and the relationship between the blood pressure signal and the pulse shape metric over a period of time may be used to determine a confidence level of the blood pressure signal. Additionally, any combination of two or more different pulse shape metrics may be used to determine a confidence level of the blood pressure signal. In some embodiments, such metrics or indirect metrics (e.g., a center of area, a rotational moment, a mean, a median, a standard deviation, kurtosis, a pulse wave area, peak to peak amplitude, a natural frequency, damping, Gaussian fit, etc.) may be related to (e.g., may be indicative of) the elasticity of the arterial system or to the change in the elasticity of the arterial system, which in turn may be correlated to the blood pressure or to the change in the blood pressure over a period of time by the Moens-Korteweg-Hughes equation. Thus, the above-disclosed methods for determining a confidence level of a blood pressure signal may be adapted to determine the confidence level based on various other metrics set forth herein. For example, if the expected correlation between changes in the damping factor and changes in the blood pressure signal are not observed, the system 10 may determine that the blood pressure signal has a low confidence level. In yet other embodiments, if the change in the damping factor varies by more than a threshold percentage from the change in the blood pressure signal obtained via the blood pressure cuff or derived from the DPTT, the system 10 may determine that the blood pressure signal has a low confidence level as described above with respect to FIGS. 4-7.

Figure 8:
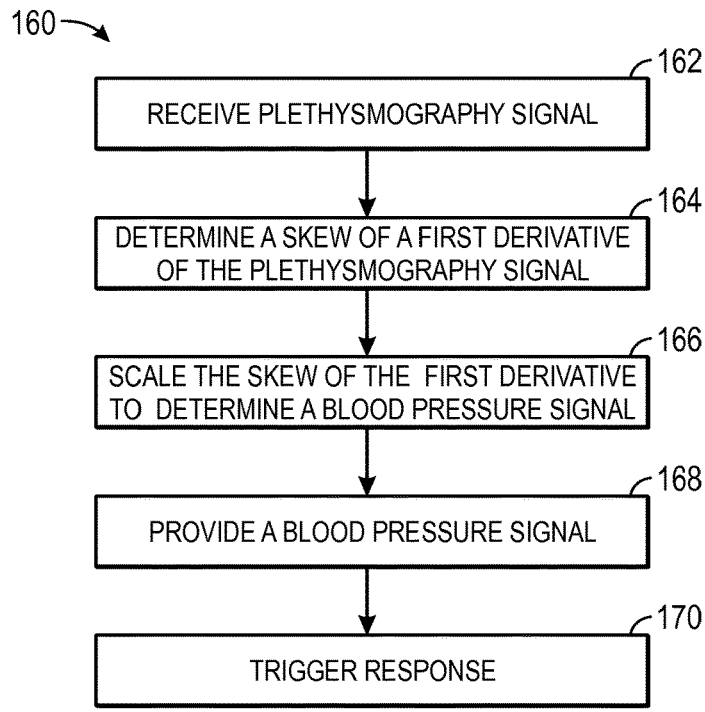
FIG. 8 is a process flow diagram of a method of monitoring blood pressure based on a skew of a first derivative, in accordance with an embodiment.

FIG. 8 is a process flow diagram illustrating an alternative method for monitoring blood pressure of a patient using the skew of the first derivative of the PPG signal. In some embodiments, blood pressure may be continuously monitored using only a single PPG signal from a single sensor 14. As illustrated in the graphs of FIG. 3, the skew metric trends with pulse pressure. As discussed above, pulse pressure is the difference between systolic pressure and diastolic pressure, and is related to a patient's blood pressure. Blood pressure is related to the amount of pressure exerted by the blood against the walls of a blood vessel, and systolic pressure is generally a pressure that is exerted when the patient's heart contracts (e.g., near the end of a stroke output of a left ventricle of the patient's heart), while diastolic pressure is generally a pressure that is exerted when the patient's heart relaxes (e.g., during ventricular diastole). Thus, monitoring the PPG signal and calculating the skew metric over a period of time can provide an indication of changes in pulse pressure, and thus, changes in blood pressure. In some embodiments, the skew metric may be displayed on a display of the monitor 12 to provide additional data related to changes in blood pressure. In certain embodiments, a baseline blood pressure may be determined, and the skew metric may be utilized to provide an indication of whether the blood pressure is increasing or decreasing over time. In some embodiments, certain actions may be triggered based on whether the skew metric changes by a certain amount (e.g., more than a threshold percentage over a period of time). For example, if the skew metric changes significantly (e.g., by 10%, 15%, 20%, 25%, or more), the system may be configured to take a blood pressure reading, to provide an alarm, and/or to provide an indication that the blood pressure is changing. As noted above, the skew metric is not influenced by changes in vasotone, and thus, in some circumstances may provide an accurate depiction of relative changes in pulse pressure and/or blood pressure.

Accordingly, as shown in FIG. 8, the skew metric may be appropriately scaled to generate blood pressure measurements or parameters related to blood pressure. The method 160 may begin when a PPG signal is received in step 162. At step 164, the skew of the first derivative of the PPG signal over time is determined. As shown in step 166, the skew of the first derivative may be appropriately scaled to determine blood pressure. For example, a linear scale factor may be applied to appropriately scale the skew to provide a blood pressure measurement. In some embodiments, the scale factor may be preprogrammed into a memory (e.g., a memory of the monitor 12 or sensor 14) based on empirical data. In certain embodiments, the scale factor may be determined for a particular patient based on a baseline measurement of the difference in pulse pressure measurements and the difference in skew measurements at a particular time. Then, the blood pressure signal or a parameter related to the blood pressure may be provided to the caregiver or user in step 168. For example, the blood pressure signal derived from the skew metric may be provided on the display of the monitor 12. Alternatively or in addition, a response may be triggered based on the blood pressure signal or changes in the blood pressure signal as shown in step 170. In some embodiments, the response may be triggered if the skew and/or the blood pressure changes by a predetermined amount or percentage over a period of time (e.g., by 5%, 10%, 15%, or more over 1 minute, 2 minutes, or longer). For example, in some embodiments, the monitor 12 may be configured to automatically initiate a new blood pressure measurement. In some embodiments, the monitor 12 may be configured to provide a message or indication relating to blood pressure may be provided on the display 24 of the monitor 12 to trigger a suitable response. In some embodiments, an indication that a new blood pressure measurement is needed, may be provided on the display 24 of the monitor 12. In some embodiments, a message instructing the user to change the patient's posture, adjust drug delivery, or initiate another suitable intervention may be provided on the display 24 of the monitor 12. Such methods and systems may advantageously facilitate blood pressure monitoring with only a single PPG sensor, thus facilitating monitoring with less hardware and/or different processing steps. Furthermore, such methods and systems may enable the determination of blood pressure without adverse affects due to changes in vasotone.

As noted above, various other metrics may be related to the elasticity of the patient's arterial system and/or to the patient's blood pressure. Thus, such metrics may also be utilized by the monitor 12 to continuously monitor the patient's blood pressure and/or pulse pressure using only a signal sensor 14. For example, in some embodiments, the metric may be any suitable pulse shape metric, such as a center of area, a rotational moment, a mean, a median, a standard deviation, kurtosis, a pulse wave area, peak to peak amplitude, a mean path ratio, notch positioning, a natural frequency (or an inverse thereof), or a damping factor. As noted above, in some embodiments, an indirect pulse shape metric, such as a Gaussian fit, may be related to the elasticity of the arterial system and/or to the blood pressure signal. Accordingly, changes in such metrics may be monitored and appropriately scaled or processed to provide an indication of the blood pressure signal, and thus, the technique set forth in FIG. 8 may be adapted to utilize such other metrics to monitor the patient's blood pressure. In some embodiments, the metrics may be correlated to the elasticity of the arterial system or to the change in the elasticity of the arterial system, which in turn may be input into the Moens-Korteweg-Hughes equation to determine or to monitor the patient's blood pressure.

Additionally, in some embodiments, changes in such metrics may be monitored and utilized to determine whether significant (e.g., clinically significant) changes in blood pressure occur. By way of example, a reference blood pressure measurement may be obtained and/or monitored via any suitable technique (e.g., via a blood pressure cuff, derived from a DPTT, etc.). In some embodiments, a reference calibration (e.g., a scaling factor) between one or more of the metrics described herein and the blood pressure signal may be determined. The reference calibration may be determined through any suitable technique, such as by monitoring a patient's blood pressure and/or one or more of the metrics over a range of blood pressures as the patient raises or lowers their hand or otherwise changes internal transmural pressures. Changes in one or more of the metrics may be monitored over a period of time, and calibrated (e.g., calibrated via the reference calibration and/or appropriately scaled) to monitor changes in blood pressure. In certain embodiments, the one or more metrics may be monitored and large changes (e.g., changes greater than a predetermined threshold, such as about more than 3%, 5%, 10%, 15%, 20%, 25%, or more, over a period of time, such as about 0.5, 1, 2, 3, or more minutes) may trigger an alarm or prompt other actions, such as prompting an operator to obtain an updated blood pressure signal via the blood pressure cuff, for example.

Figure 9:
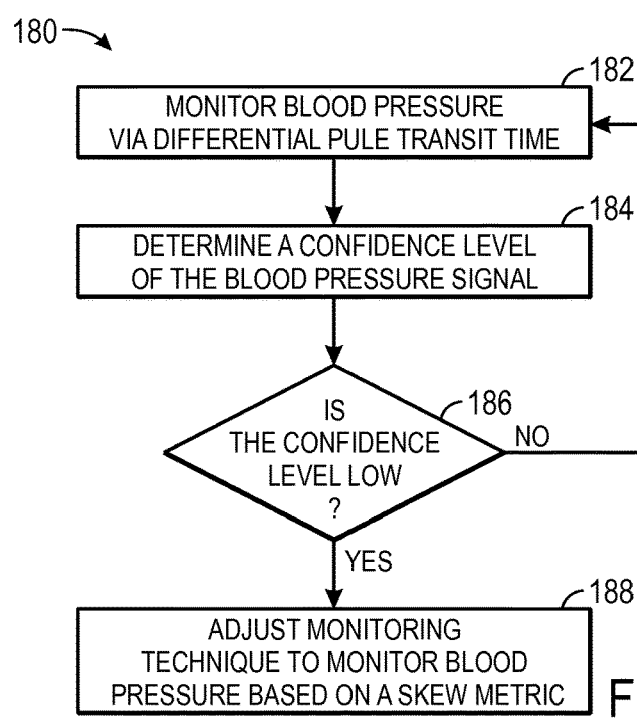
FIG. 9 is a process flow diagram illustrating a method for monitoring blood pressure of a patient using multiple different monitoring techniques, in accordance with an embodiment.

In some embodiments, the system 10 may be configured to utilize various combinations of the methods for blood pressure monitoring provided herein. FIG. 9 is a process flow diagram illustrating a method for monitoring blood pressure of a patient using multiple different monitoring techniques. As shown in step 80, the system 10 may monitor blood pressure based on the DPTT or via another suitable blood pressure monitoring device. For example, the system 10 may monitor the patient's blood pressure in accordance with method 80 of FIG. 4. In step 82, the system 10 may determine a confidence level of the blood pressure signal via any suitable technique or using any suitable metric. If it is determined that the blood pressure signal has a low confidence level at step 84, the system 10 may adjust (e.g., switch, change, etc.) monitoring modes and/or may begin to determine the blood pressure based on the skew metric (e.g., as set for in the method 160 of FIG. 8) so as to avoid the adverse effects due to changes in vasotone. The system 10 may temporarily change monitoring techniques for a predetermined amount of time, or the system may change monitoring techniques until prompted or instructed by a user input. In some embodiments, the user or caregiver may be able to select a preferred monitoring method based on various factors, such as the user's preferences, the patient's needs, or based on whether the patient is being administered medication that may cause changes in vasotone. For example, the patient's blood pressure may be monitored via method 80, and the user may provide an input to change the monitoring method to method 160 if certain medications that affect vasotone are being administered to the patient.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims. Further, it should be understood that certain elements of the disclosed embodiments may be combined or exchanged with one another.

What is claimed is:

1. A patient monitor configured to monitor blood pressure comprising:
a memory storing instructions for:
receiving a plethysmography signal representative of one or more patient parameters;
determining a change in a pulse shape metric of the plethysmography signal;
generating a blood pressure signal based on the plethysmography signal;
determining a change in the blood pressure signal over a period of time;
determining a confidence level of the blood pressure signal based at least in part on a correlation between the change in the blood pressure signal and the change in the pulse shape metric over the period of time, wherein the confidence level is determined to be a low confidence level based on an inverse correlation between the change in the blood pressure signal and the change in the pulse shape metric; and
in response to determining the confidence level is the low confidence level, switching from determining a blood pressure via a first monitoring mode to determining a blood pressure via a second monitoring mode different from the first monitoring mode; and
a processor configured to execute the instructions.

2. The patient monitor of claim 1, wherein the pulse shape metric is a skew of a first derivative of the plethysmography signal.

3. The patient monitor of claim 1, wherein the memory stores instructions for determining a high confidence level of the blood pressure signal if the blood pressure signal and the pulse shape metric change in the same direction and a difference between the change in the blood pressure signal and the change in the pulse shape metric is within a predetermined tolerance.

4. The patient monitor of claim 3, wherein the processor is configured to instruct a display of the patient monitor to provide the blood pressure signal if a high confidence level is determined.

5. The patient monitor of claim 1, wherein the memory stores instructions for discarding the blood pressure signal received over the period of time if the low confidence level is determined.

6. The patient monitor of claim 1, wherein the blood pressure signal is generated based on a differential pulse transit time.

7. The patient monitor of claim 1, comprising light drive circuitry configured to drive a respective light emitter of the plethysmography sensor to emit light into a subject's tissue to enable generation of the plethysmography signal.

8. A method for determining a confidence level of a blood pressure signal comprising:
using a processor:
receiving a blood pressure signal;
receiving a plethysmography signal;
determining a change in the blood pressure signal over a period of time;
determining a change in a pulse shape metric of the plethysmography signal over the period of time;
determining the confidence level based on whether there is an expected correlation between the change in the blood pressure signal and the change in the pulse shape metric over the period of time, wherein the confidence level is determined to be a low confidence level upon a determination that the expected correlation is not present; and
in response to determining the confidence level is the low confidence level, switching from determining a blood pressure via a first monitoring mode to determining a blood pressure via a second monitoring mode different from the first monitoring mode.

9. The method of claim 8, wherein the pulse shape metric is a skew of a first derivative of the plethysmography signal.

10. The method of claim 8, comprising determining a high confidence level of the blood pressure signal and providing an indication of the high confidence level on a display, in response to the expected correlation being present and a difference between the change in the blood pressure signal and the change in the pulse shape metric being within a predetermined tolerance, using the processor.

11. The method of claim 8, comprising providing a prompt to initiate another blood pressure measurement via a speaker or a display in response to determining the confidence level is the low confidence level, using the processor.

12. The method of claim 8, wherein determining the blood pressure via the first monitoring mode comprises determining the blood pressure based on a differential pulse transit time, and wherein determining the blood pressure via the second monitoring mode comprises determining the blood pressure based on a skew of a first derivative of the plethysmography signal.

13. A system for monitoring blood pressure comprising:
one or more plethysmography sensors configured to obtain one or more plethysmography signals;
a monitor comprising circuitry configured to:
receive the one or more plethysmography signals;
generate a blood pressure signal based on the one or more plethysmography signals;
calculate a change in the blood pressure signal over a period of time;
calculate a change in a pulse shape metric of a plethymography signal of the one or more plethysmography signals over the period of time;
compare the change in the blood pressure signal to the change in the pulse shape metric over the period of time to determine a degree of correlation;
determine a confidence level of the blood pressure signal over the period of time based at least in part on the degree of correlation, wherein the confidence level is determined to be a low confidence level based on an inverse correlation between the change in the blood pressure signal and the change in the pulse shape metric; and
in response to determining the confidence level is the low confidence level, switch from determining a blood pressure via a first monitoring mode to determining a blood pressure via a second monitoring mode different from the first monitoring mode.

14. The system of claim 13, wherein the pulse shape metric is a skew of a first derivative of the plethysmography signal.

15. The system of claim 14, wherein the monitor is configured to determine a high confidence level of the blood pressure signal if the blood pressure signal and the skew of the first derivative of the plethysmography signal change in the same direction and a difference between the change in the blood pressure signal and the change in the skew of the first derivative is within a predetermined tolerance range.

16. The system of claim 14, wherein the monitor is configured to monitor blood pressure based on a scaled skew of the first derivative of the plethysmography signal in response to determining the confidence level is the low confidence level.

17. The system of claim 13, wherein each of the one or more plethysmography sensors comprise a respective emitter configured to provide light to a subject's tissue and a respective detector configured to generate a respective plethysmography signal of the one or more plethysmography signals based on light that passed through the subject's tissue.

18. The system of claim 13, wherein the monitor is configured to disable a blood pressure alarm in response to determining the confidence level is the low confidence level.

* * * * *